(12) United States Patent
Clark

(10) Patent No.: US 12,239,566 B1
(45) Date of Patent: Mar. 4, 2025

(54) PENIS ENLARGEMENT DEVICE

(71) Applicant: Ben Clark, Flintstone, GA (US)

(72) Inventor: Ben Clark, Flintstone, GA (US)

( * ) Notice: Subject to any disclaimer, the term of this patent is extended or adjusted under 35 U.S.C. 154(b) by 0 days.

(21) Appl. No.: 18/430,985

(22) Filed: Feb. 2, 2024

(51) Int. Cl.
  *A61F 5/41* (2006.01)

(52) U.S. Cl.
  CPC .......... *A61F 5/41* (2013.01); *A61F 2005/414* (2013.01)

(58) Field of Classification Search
  CPC .... A61F 5/41; A61F 2005/414; A61F 2/0004; A61F 2/0009; A61F 2/0031; A61F 2/0054; A61B 17/122
  See application file for complete search history.

(56) References Cited

U.S. PATENT DOCUMENTS 5,599,275 A * 2/1997 France ...................... A61F 5/41
  600/38
6,033,374 A * 3/2000 Miller, Jr. ............ A61H 1/0218
  602/61
6,398,720 B1 * 6/2002 Dabal ....................... A61F 5/41
  600/38
2006/0270533 A1 * 11/2006 Dana ........................ A61F 5/41
  482/105

FOREIGN PATENT DOCUMENTS

WO   WO 2021/209076   * 10/2021 ............. A61H 19/30

* cited by examiner

*Primary Examiner* — Carrie R Dorna
(74) *Attorney, Agent, or Firm* — Sam Pierce

(57) ABSTRACT

According to an aspect of the present invention, there is provided a device for enlargement of the penis of a user, comprising: a first part configured for contacting the penis of a user at a central portion of the first part and a second part configured for contacting the penis of a user at a central portion of the second part; a hinge connecting the first part and the second part at a first end of the first part and a first end of the second part, wherein the hinge is configured to close around the penis of a user; an adjustable bolt and wingnut, wherein the device is adjustable to a variety of widths by the adjustable bolt and wingnut; and one or more weights are attached to the device to apply a stretching force to the penis of a user.

2 Claims, 2 Drawing Sheets

PENIS ENLARGEMENT DEVICE

BACKGROUND

Methods and devices for enhancing the penis of a male individual are well-known in the patent literature.

For example, US20150202109 discloses a penis enlargement device comprising a substantially flat member with a hole and neck adapted to fit over a human penis to be positioned flat against a user's lower abdomen; a ring member also adapted to fit around the base of the penis; a waist strap attached to said flat member adapted to hold the flat member in place; a substantially cylindrical cover attached to said neck adapted to connect to either stretch cords or to a weight container; whereby, weight or force is applied to the base of the penis causing the penis to enlarge over time.

U.S. Pat. No. 7,802,577 discloses a harness for stretching the penis, includes a belt for encircling the waist of the user, with a fastening mechanism secured to a rear part of the belt. A first tractive means applies tractive forces at the base of the penis of a user of the harness, and is secured to the belt via the fastening mechanism. A second tractive means applies tractive forces at the edge of the head of the penis of a user of the harness, and is also secured to the belt via the fastening mechanism. The first tractive means and the second tractive means apply a stretching force to the penis of the user of the harness.

U.S. Pat. No. 8,075,473 discloses an extension device for permanent penis enlargement and straightening via long-term elongation, the extension device comprising: a fastening means for application to a penis, the fastening means having an accommodation body, the accommodation body: being dimensionally stable, accommodating a glans penis of the penis over the entire surface of the glans penis when the glans penis is inserted into the extension device, having an inner contour essentially corresponding to a shape of the glans penis, having an opening for allowing insertion of the glans penis, and having an inner surface; a pulling apparatus connected to the fastening means; an elastic tube seal connected to the opening of the accommodation body; and a lubricant located on the inner surface of the accommodation body; wherein the pulling apparatus is formed by: a support, strap, belt or other clothing accessory or piece of clothing, the support, strap, belt or other clothing accessory or piece of clothing being connected to the accommodation body, being held on a body of the user, and being used as a stop, a stationary object, a frame supported on a body of the user, the frame being adjustable in length, or a weight attached to the accommodation body.

Nonetheless, prior art methods and devices suffer from significant drawbacks, including pain and lack of efficacy in bringing about the desired penile enlargement.

SUMMARY OF INVENTION

Therefore, the present invention provides an improved device for enlarging the penis of a user which does not require the use of vacuum cups with the attendant risk of edema and which requires reduced time to achieve a result compared to prior art devices.

According to one aspect of the present invention disclosed herein, there is provided a device for enlargement of the penis of a user, comprising: a first part configured for contacting the penis of a user at a central portion of the first part and a second part configured for contacting the penis of a user at a central portion of the second part; a hinge connecting the first part and the second part at a first end of the first part and a first end of the second part, wherein the hinge is configured to close around the penis of a user; an adjustable bolt and wingnut, wherein the device is adjustable to a variety of widths by the adjustable bolt and wingnut; and one or more weights are attached to the device to apply a stretching force to the penis of a user.

According to one of yet another aspects of the present invention disclosed herein, there is provided a method of enlarging the penis of a user, comprising:

DETAILED DESCRIPTION

The present invention relates to an apparatus for stretching of human tissue, and in particular the penis. The present invention utilizes weights to accomplish stretching of the penis.

A significant percentage of the male population is dissatisfied with the length of their penis. The length of a man's penis is given considerable significance relative to his ability to satisfy his partner during intercourse. Men with shorter than average penises are subject to ridicule and a corresponding amount of self-doubt and lack of confidence.

Recently, methods have been developed to enlarge the penis. These methods, however, are surgical in nature, usually requiring the injection of fat from another part of the body. Such procedures run the same risks attendant to all surgery, infection, complications, and adverse reactions to drugs used during the procedure, to name a few. Furthermore, such procedure, if effective at all, are better at increasing the circumference of the penis as opposed to the length. In addition, the degree of permanence of any change is doubtful.

These and other deficiencies of the prior art are addressed by the present invention which is directed to an apparatus for stretching human tissue of the male gender, and specifically penis. The apparatus is an adjustable device that is fitted to the penis to effectuate permanent elongation of the penis.

An object of the present invention is to provide an apparatus for effectuating permanent elongation of the penis.

Another object of the present invention is to provide a device for elongating a penis which does not require an invasive procedure such as surgery.

An embodiment illustrative of the present invention will be described with reference to the attached drawings.

Figure 1:
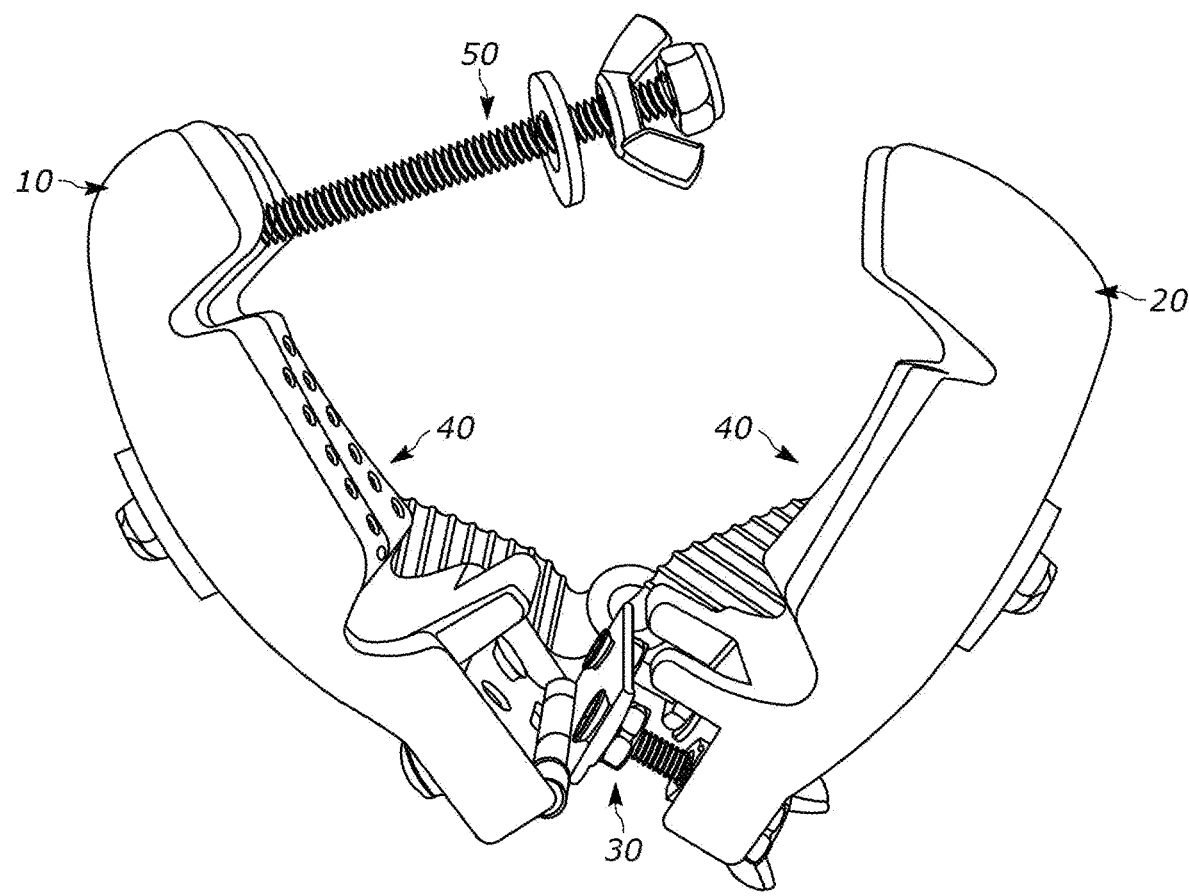
FIG. 1 illustrates a penis enlargement device according to an embodiment of the present invention in open position.

FIG. 1 illustrates a penis enlargement device according to an embodiment of the present invention in open position.

In FIG. 1, two polymer parts 10 and 20 which are joined by a hinge 30 are shown in open position. Parts 10 and 20 can be opened to fit the device around a penis, and the hinge 30 allows the parts 10 and 20 to be closed about the circumference of the penis. The inner diameter of parts 10 and 20 are chosen so that the device will fit penises of various diameters.

The internal surfaces 40 of each part 10 and 20 are designed to grip the penis in ergonomic manner when in the closed position.

An adjustable bolt and wingnut 50 is provided at the top of each of the parts 10 and 20 to accommodate adjustment of the device.

Figure 2:
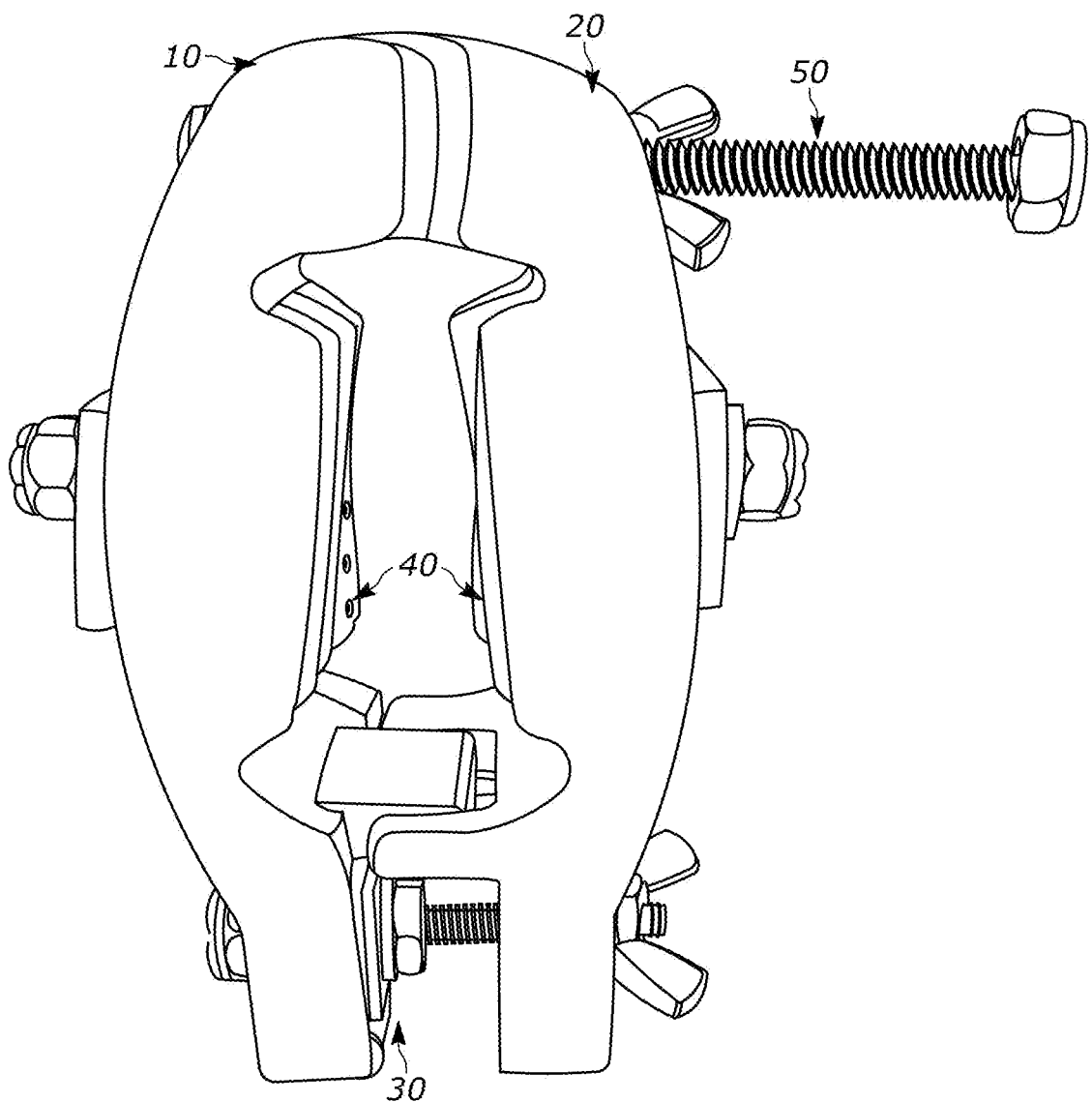
FIG. 2 illustrates a penis enlargement device according to an embodiment of the present invention in closed position.

FIG. 2 illustrates a penis enlargement device according to an embodiment of the present invention in closed position.

In FIG. 2, the polymer parts 10 and 20 which are joined by a hinge 30 are closed around the penis in the closed position of the device. Parts 10 and 20 can be opened to fit the device around a penis, and the hinge 30 allows the parts 10 and 20 to be closed about the circumference of the penis. The inner diameter of parts 10 and 20 are chosen so that the device will fit penises of various diameters. The internal surfaces 40 of each part 10 and 20 are designed to grip the penis in ergonomic manner when in the closed position. An adjustable bolt and wingnut 50 is provided at the top of each of the parts 10 and 20 to accommodate adjustment of the device.

When the device is secured to the penis of the user, one or more weights can be attached to the device to apply a stretching force to the penis of the user.

The embodiments described above are given merely for example and for the purpose of facilitating the understanding of the present invention and are not intended to limit the interpretation of the present invention. The respective elements and their arrangements, materials, conditions, shapes, sizes, or the like of the embodiment are not limited to the illustrated examples but may be appropriately changed. Further, the constituents described in the embodiment may be partially replaced or combined together.

What is claimed is:

1. A device for enlargement of a penis of a user, comprising:
   a first part with a plurality of indentations configured for contacting the penis of the user at a central portion of the first part, wherein the central portion of the first part is demarcated on either side by a U-shaped depression;
   a second part configured for contacting the penis of the user at a central portion of the second part on the opposite side of the penis from the first part, wherein the central portion of the second part is demarcated on either side by a U-shaped depression;
   a hinge with a first adjustable bolt and wingnut connecting the first part and the second part at a first end of the first part and a first end of the second part, wherein the hinge is configured to close around the penis of the user;
   a second adjustable bolt and wingnut attached to a second end of the second part separated from the first end of the second part by the central portion of the second part, wherein the device is adjustable to a variety of widths by the second adjustable bolt and wingnut; and
   one or more weights are attached to the device and are configured to apply a stretching force to the penis of the user.

2. The device for enlargement of the penis of the user of claim 1, wherein one or more screws, the first adjustable bolt and wingnut, and the second adjustable bolt and wingnut are configured for retaining the first and second parts in a closed position.

* * * * *